United States Patent [19]

Havran

[11] Patent Number: 5,282,479
[45] Date of Patent: Feb. 1, 1994

[54] GUIDEWIRE INTRODUCER WITH GUIDEWIRE GRASP AND RELEASE MEANS

[75] Inventor: Geary A. Havran, Tampa, Fla.

[73] Assignee: BOC Health Care, Inc., New Providence, N.J.

[21] Appl. No.: 959,867

[22] Filed: Oct. 13, 1992

[51] Int. Cl.⁵ .............................................. A61B 5/00
[52] U.S. Cl. .................................. 128/772; 604/171
[58] Field of Search ............... 128/657, 772; 403/93, 403/94, 109; 604/165, 171, 280

[56] References Cited

U.S. PATENT DOCUMENTS

| | | | |
|---|---|---|---|
| 1,481,981 | 1/1924 | Boye | 403/109 |
| 4,230,110 | 10/1980 | Beroff . | |
| 4,235,232 | 11/1980 | Spaven et al. . | |
| 4,299,421 | 11/1981 | Bontrager | 403/109 |
| 4,917,094 | 4/1990 | Lynch et al. | 128/772 |
| 4,957,117 | 9/1990 | Wysham | 128/772 |
| 5,113,872 | 5/1992 | Jahrmarkt et al. | 128/772 |
| 5,125,905 | 6/1992 | Wright et al. | 128/772 |

*Primary Examiner*—Max Hindenburg
*Attorney, Agent, or Firm*—Roger M. Rathbun; Larry R. Cassett

[57] ABSTRACT

A combination of a protective tube and guidewire straightener used to locate a guidewire into a patient for introducing a catheter into a patient's bloodvessel. The guidewire straightener has a flexible end that flexes inwardly to lock the guidewire in a fixed position within the protective tube. The protective tube has an opening so that the guidewire straightener can be rotated by the user to align the flexible end with the opening to allow the flexible end to be released outwardly to unlock the guidewire so that it can move within the protective tube. A further opening in the shape of an elongated slot is formed in the protective tube and which allows the user to move the guidewire to advance or retract the guidewire from the protective tube. The positioning of the components are such that a user, by the manipulation of only one hand, can unlock the guidewire from it's fixed position and advance it into the patient, leaving the user's other hand free to carry out other operations.

6 Claims, 3 Drawing Sheets

GUIDEWIRE INTRODUCER WITH GUIDEWIRE GRASP AND RELEASE MEANS

BACKGROUND OF THE INVENTION

This invention relates to medical guidewires and to a means of removing such guidewires from the protective tubes in which guidewires are shipped and for the insertion of the guidewires into patients through a one hand operation.

Guidewires are routinely used in medical procedures where it is desired to introduce a catheter into a patient's blood vessel such as an artery or vein.

In a typical procedure, one approach of utilizing such guidewires for the positioning of a catheter is called the Seldinger technique. In that technique, a catheter introducer is used that has a relatively short flexible cannula that is placed within the patient's blood vessel. Actual insertion of the cannula is assisted by the use of a needle that is positioned within the cannula and is thus inserted in the blood vessel. Upon insertion, the needle is withdrawn, leaving the cannula tip within the blood vessel while the body of the catheter introducer remains external of the patient.

A guidewire is then inserted through the catheter introducer and is extended through the tip of the cannula within the patient's blood vessel until it is positioned with its tip at the desired location within the patient. Upon removal of the catheter introducer, the guidewire remains in the patient and a long catheter is easily slid over the guidewire to the desired position and the guidewire withdrawn. Thus, the catheter remains within the patient having its distal end located at the proper position within the patient's blood vessel.

Such guidewires are delivered through normal shipping channels and are subject to considerable handling prior to and during shipment. The guidewire itself is packaged within a protective tube in a coiled form. Generally, a guidewire straightener fits within the end of the protective tube and the guidewire itself passes through the guidewire straightener and has its end formed into a J configuration just outside the distal end of the guidewire straightener.

A guidewire straightener, of the type used herein, is shown and described in U.S. Pat. No. 5,125,905 and assigned to the present assignee. A difficulty arises, however, in the actual introduction of the guidewire into the patient using the configuration of that patent. The guidewire requires the manipulation of two hands for the user to move the guidewire and extend it from the protective tube into the patient's blood vessel.

In using the arrangement shown in the aforementioned patent, the user is required to grip the protective tube with one hand and pull the guidewire and guidewire straightener out from that tube with the other hand. Thus, the user needs both hands to properly introduce the guidewire, whereas, it is more advantageous for the user to have a free hand to carry out other operations during such introduction. Continued insertion of the guidewire requires both hands as the guidewire is advanced into the patient in increments.

As an alternate to introducing the guidewire in increments, some users chose to remove the entire guidewire at one time from the protective tube and then introduce it into the patient. Again, however, a difficulty is encountered in that the lengthy proximal end of the guidewire swings free as the distal end is introduced into the patient and that proximal end may easily touch some nonsterile object and thus the guidewire itself is no longer sterile.

SUMMARY OF THE INVENTION

The present invention provides an improved combination of a guidewire straightener amd protective tube that overcomes the aforesaid diffriculties by allowing the guidewire to be progressed forwardly from the protective tube into the patient by the manipulation of but one hand of the user.

The guidewire straightener is almost identical to the straightener of the U.S. Pat. No. 5,125,905, however the guidewire may be introduced into the patient without removal of the guidewire straightener from the end of the protective tube. Additionally, the guidewire can be moved within the protective tube in the forward or reverse direction by the manipulation of only one hand of the user. As noted in the aforementioned patent, the guidewire straightener has a plurality of flexible tabs that are compressed about the guidewire as the guidewire straightener is fitted on to the end of the protective tube.

As one feature of the present invention, therefore, the protective tube includes a plurality of openings, preferable the same number as the number of flexible tabs on the guidewire straightener, and those openings can align with the flexible tabs when the guidewire straightener is rotated within the protective tube into the proper position. When, therefore, the flexible tabs are aligned with the openings, the tabs are free to move outwardly or become uncompressed about the guidewire such that the guidewire is free to move within the protective tube. Accordingly, by simple rotation of the guidewire straightener, the guidewire may be locked, or unlocked, in it's position within the protective tube.

As can be seen, therefore, the user can, by the use of only one hand, lock and unlock the guidewire within the protective tube and it is not necessary to use a second hand to actually remove the guidewire straightener from the end of the protective tube.

In a second feature of the present invention, an elongated slot is provided in the protective tube and which enables the user to use one finger to advance or retract the guidewire within the protective tube. Preferable the thumb is used and is, of course, on the same hand as used to rotate the guidewire straightener to it's desired position.

Accordingly, the present combination of guidewire straightener and protective tube allows the user to both unlock the guidewire within the protective tube but also to enable the user to use that same hand to insert the guidewire into the patient and, when desired, to retract the guidewire from the patient and back into the protective tube.

DESCRIPTION OF THE PREFERRED EMBODIMENT

Figure 1:
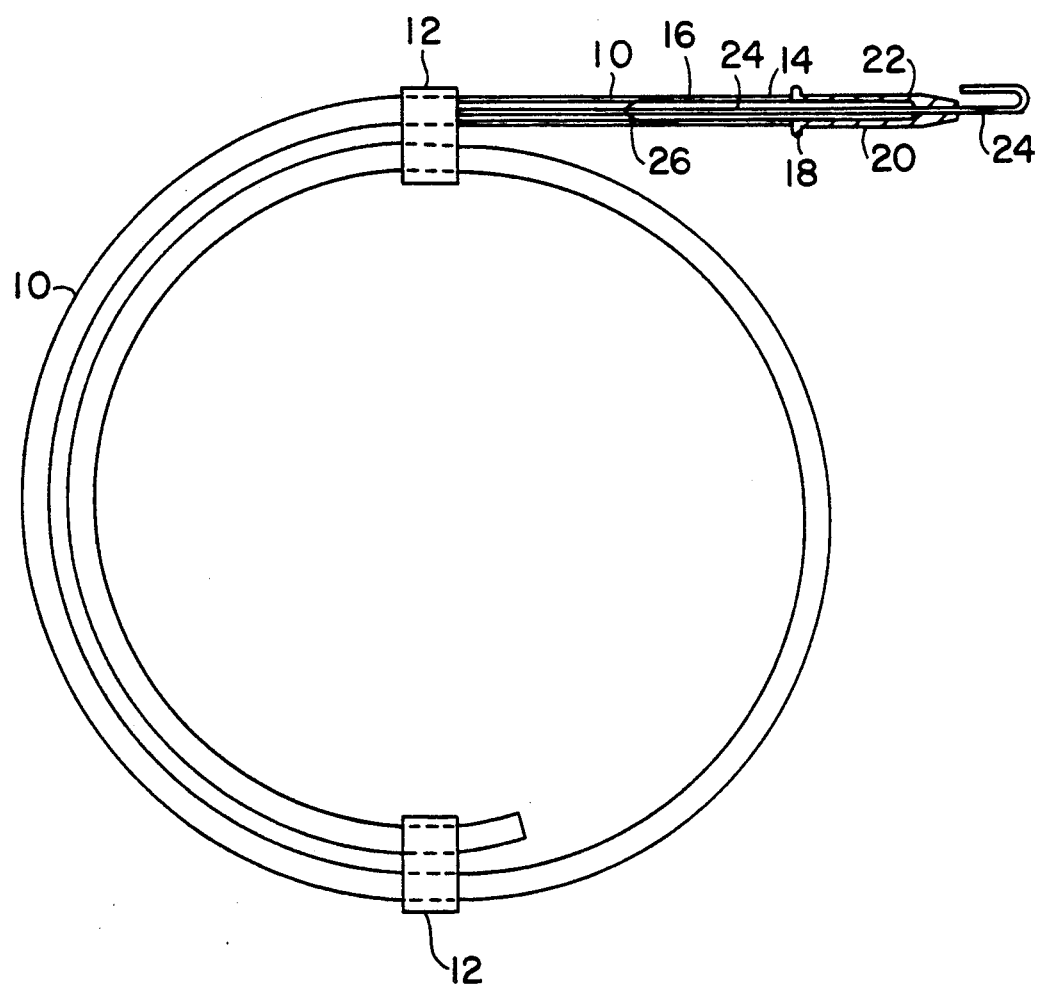
FIG. 1 is a plan view, partly in section, of a guidewire contained within a protective tube and having a guidewire straightener constructed generally in accordance with the invention of the prior art patent.

Referring now to FIG. 1, there is shown a plan view, partly in section of a typical guidewire assembly in the form it is shipped to customers.

A protective plastic tube 10 is coiled within the shipping package and is constrained in the coiled position by means such as a pair of retainers 12. Generally, a sealed package surrounds the plastic tubing and the contents sterilized prior to shipment.

A guidewire straightener 14 is affixed to the distal end of the protective plastic tube 10. In a normal manner, that affixation is by a force fit between the internal diameter of a projecting cylindrical hub 16 formed as part of the guidewire straightener 14. A peripheral flange 18 is also formed as part of the guidewire straightener 14 and, when fitted on to the end of the protective plastic tube 10, the peripheral flange 18 abuts the distal end thereof. The remaining part of the guidewire straightener 14 is a body 20 that is molded to fit within a catheter introducer as will be later explained.

A passageway 22 is formed in the guidewire straightener 14 and through which passes the guidewire 24. As seen in the FIG. 1, the guidewire 24 projects outward from the body 20 and is configured in a J-shape.

At the inner end of cylindrical hub 16, there is formed a flexible end 26 that is designed to flex inwardly as the guidewire straightener 14 is affixed to the distal end of protective plastic tube 10 and which serves to grip the guidewire 24, as will be explained, to prevent its movement within the protective plastic tube 10 during shipping and handling.

Figure 2:
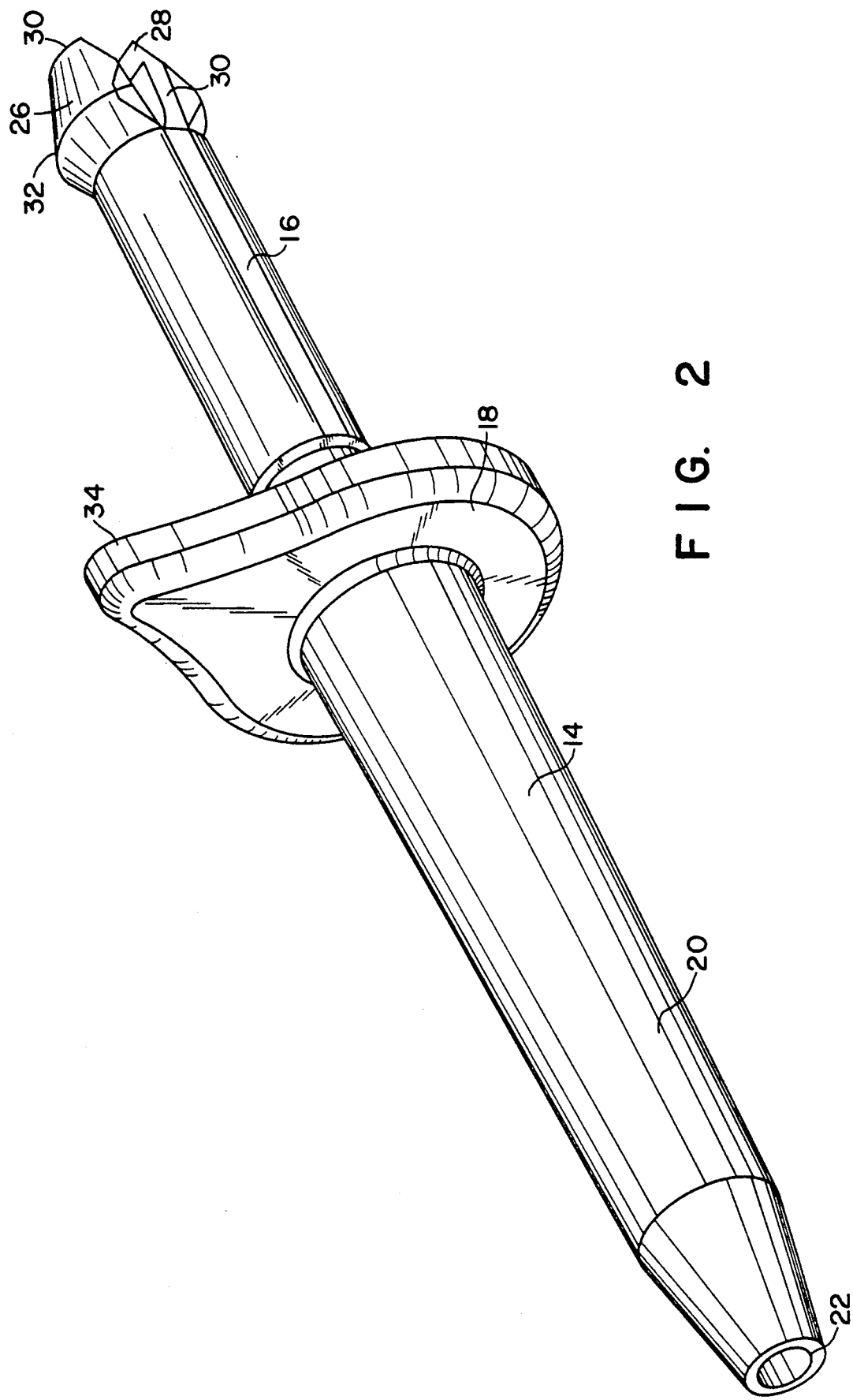
FIG. 2 is an isometric view of a guidewire straightener constructed specifically for the present invention.

Turning now to FIG. 2 there is shown an isometric view of a guidewire straightener 14 useable with the present invention to straighten the J-shaped end of a guidewire 24 prior to introduction into the blood vessel of a patient. As may be seen in FIG. 2, flexible end 26 includes a slot 28 formed therein creating a bifurcated end having two flexible tabs 30. As can be seen, although there are only two flexible tabs 30 shown in the preferred embodiment, other numbers of tabs could be formed. Surrounding the slot 28 is an enlarged diameter ridge 32 of predetermined diameter such that insertion of the guidewire straightener 14 into the protective tube 10 (FIG. 1) causes the flexible end 26 to pinch inwardly and grip the guidewire (FIG. 1).

Thus, the guidewire straightener 14 is a single piece molded of a flexible plastic, such as polypropylene, and which, when assembled to its protective plastic tube, captures the guidewire and thus prevents migration of the guidewire within the protective plastic tube during packaging, handling and shipping. Also included on the guidewire straightener 14 is a projection 34 that is easily engaged by a user's finger and the use of which will be later explained.

When installed on the end of protective plastic tube 10, however, the flexible end 26, having the enlarged diameter ridge 28 that is larger than the inner diameter of protective plastic tube 10 by a predetermined amount, is compressed inwardly and grips the guidewire 24.

Figure 3:
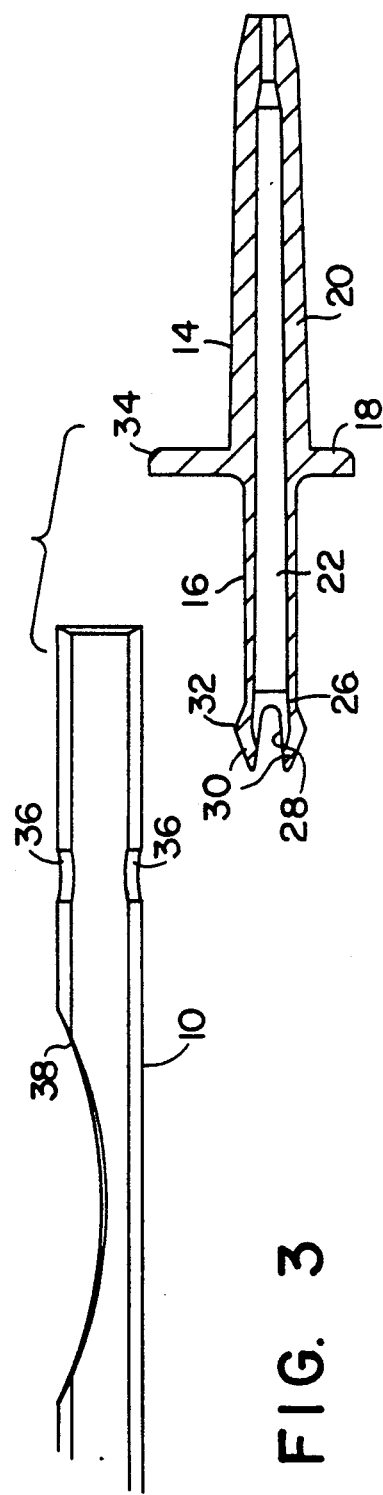
FIG. 3 is a cross-sectional view of a guidewire straightener positioned to be affixed to the end of a protective tube.

Turning now to FIG. 3, there is shown a cross-sectional view of a guidewire straightener 14 positioned to be inserted into the open end of protective plastic tube 10. As can be seen, protective plastic tube 10 includes a pair of openings 36. Again, it should be noted that although two openings 36 are shown, any number of openings could be utilized providing there are a sufficient number to accept each of the flexible tabs 30 formed in the flexible end 26 of guidewire straightener 14. Further shown is an elongated slot 38 the purpose of which will be later explained.

Figure 4:
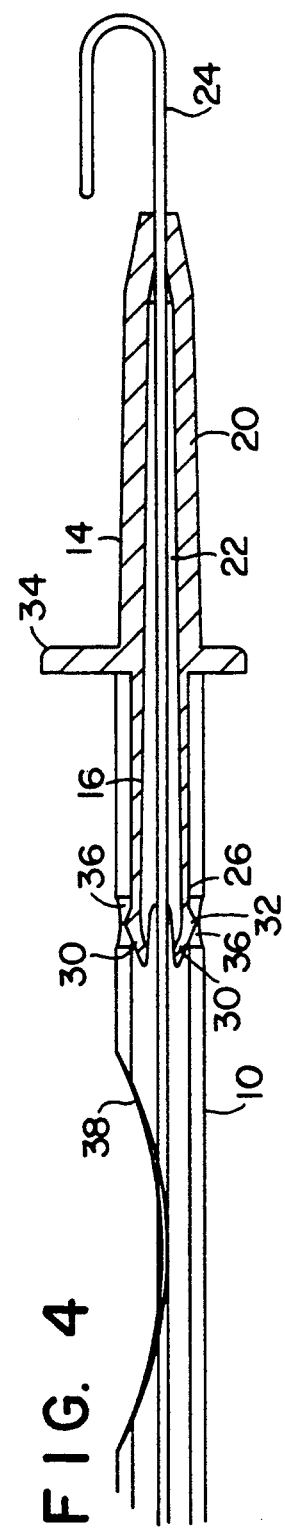
FIG. 4 is a cross-sectional view of the combination guidewire straightener and protective tube constructed in accordance with the present invention wherein the guidewire is in the unlocked position.

In FIG. 4, there is shown a cross-sectional view of a guidewire straightener 14 affixed to the end of protective plastic tube 10. In this Fig., the enlarged diameter ridge 32 of the flexible tabs 30 has expanded such that the flexible end 26 no longer grips or locks the guidewire 24 in position within protective plastic tube 10. Accordingly, it may be seen that when the enlarged diameter ridge 32 of flexible tabs 30 are aligned with the openings in protective plastic tube 10, the flexible end 26 expands, thus it's grip on the guidewire 24 is relaxed so that the guidewire 24 is free to move within protective plastic tube Also noted in FIG. 4 is elongated slot 38 and which is positioned so that a user can readily use a digit, such as the thumb, to advance or retract the guidewire with respect to protective plastic tube 10.

Figure 5:
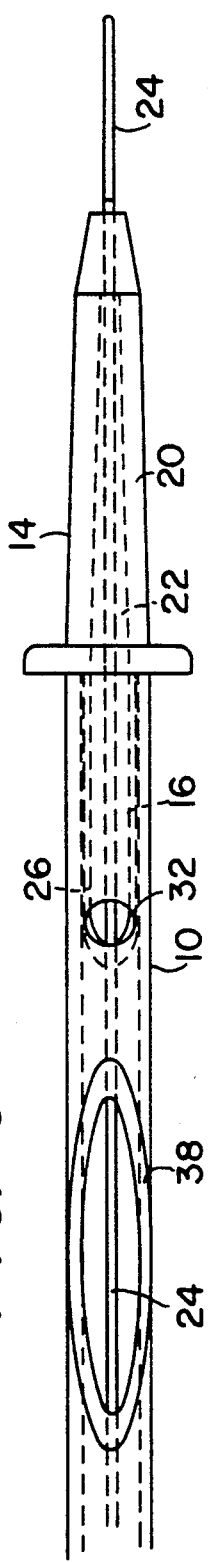
FIG. 5 is a plan view of the combination as shown in FIG. 4 wherein the guidewire is in the locked position.

Turning finally to FIG. 5, there is shown a plan view of the arrangement of FIG. 4 with the guidewire 24 locked into position within the protective plastic tube 10.

As can be seen, the guidewire straightener 14 has been rotated such that the enlarged diameter ridge 32 of flexible tabs 30 no longer align with openings 36 in protective plastic tube 10. Therefor, the flexible end 26 is compressed within protective plastic tube 10 and locks or grips the guidewire 24 holding it in position within protective plastic tube 10 in a manner described with respect to U.S. Pat. No. 5,125,905.

The overall use of the combination of protective plastic tube 10 and guidewire straightener 14 can now be explained. The arrangement is received by the user as shown in FIG. 5 with the guidewire 24 locked during transit and handling within the protective plastic tube 10. The user, by gripping the protective plastic tube 10 with one hand, can extend a finger and engage projection 34 and use it to rotate guidewire straightener 14 until the enlarged diameter ridges 32 of flexible tabs 30 align with openings 36 in protective plastic tube 10. Upon reaching such alignment, flexible tabs 30 are free to move outwardly, thereby releasing their grip on guidewire 24 to free it for movement within protective plastic tube 10.

Since the guidewire 24 is free to move, the user, still using the same hand, can directly touch and move the guidewire 24 through elongated slot 38. Thus, the user can move the guidewire 24 to extend the guidewire 24 from protective plastic tube 10 or retract the guidewire 24 back into protective plastic tube 10 and the entire operation from setting up the arrangement to inserting the guidewire 24 into a patient can conveniently be carried out by the user's one hand, leaving the other hand free to carry out other tasks.

What I claim is:

1. A combination protective tube and guidewire straightener, said guidewire straightener fitted within the inner diameter of said protective tube, said guidewire straightener having a through passageway for containing a guidewire and a cylindrical hub having an end having at least one flexible tab, said at least one flexible tab having a predetermined outer diameter normally greater than the inner diameter of said protective tube and being force fitted within the inner diameter of the protective tube to constrict said at least one flexible tab inwardly to grasp the guidewire, said protective tube having at least one opening adapted to align with said at least one flexible tab when rotated to a position to allow said at least one flexible tab to move outwardly and release the grasp on the guidewire.

2. A combination as defined in claim 1 wherein said at least one flexible tab comprises two tabs and said at least one opening in said protective tube comprises at least two openings.

3. A combination as defined claim 1 wherein said guidewire straightener further includes a projection adapted to be readily moved by a user to rotate said guidewire straightener.

4. A combination protective tube having an inner diameter and a guidewire straightener fitted within said inner diameter, said guidewire straightener having a through passageway for containing a guidewire and a hub having at least one flexible tab normally having an outer diameter greater than the inner diameter of said protective tube whereby said at least one flexible tab is compressed inwardly to lock said guidewire in a fixed position within said protective tubes said protective tube having at least one opening adapted to align with said at least one flexible tab to cause said flexible tab to unlock and release said guidewire for movement within said flexible tube, said flexible tube further having an elongated slot allowing a user to move said guidewire within said protective tube when in said unlocked status.

5. A combination as defined in claim 4 wherein said at least one opening and said elongated slot are one contiguous opening in said protective tube.

6. A combination as defined in claim 4 wherein said guidewire straightener can be rotated to a unlocked position and the guidewire moved within said protective tube by the use of one hand of a user.

* * * * *